United States Patent

Evans et al.

[11] Patent Number: 5,948,731
[45] Date of Patent: Sep. 7, 1999

[54] HERBICIDALLY-ACTIVE FATTY ACID SALTS

[75] Inventors: Steven L. Evans; John Harvey, both of San Diego, Calif.; Yasuko Tsujino, Kanagawa, Japan

[73] Assignee: Mycogen Corporation, San Diego, Calif.

[21] Appl. No.: 08/962,191

[22] Filed: Oct. 31, 1997

Related U.S. Application Data

[63] Continuation of application No. 08/458,546, Jun. 2, 1995, Pat. No. 5,703,019, which is a continuation of application No. 08/385,218, Feb. 8, 1995, abandoned, which is a continuation of application No. 07/796,161, Nov. 22, 1991, abandoned.

[51] Int. Cl.$^6$ .................................................. A01N 37/02
[52] U.S. Cl. ............................................................ 504/320
[58] Field of Search .............................................. 504/320

[56] References Cited

U.S. PATENT DOCUMENTS

| | | | |
|---|---|---|---|
| 2,626,862 | 1/1953 | Zimmerman et al. | 71/2.7 |
| 4,719,084 | 1/1988 | Schmid et al. | 422/16 |
| 4,975,110 | 12/1990 | Puritch et al. | 71/113 |
| 5,035,741 | 7/1991 | Puritch et al. | 71/113 |
| 5,196,044 | 3/1993 | Caulder et al. | 504/127 |

FOREIGN PATENT DOCUMENTS

| | | |
|---|---|---|
| 0147976 | 12/1984 | European Pat. Off. . |
| 59-199606 | 11/1984 | Japan . |
| 59-199608 | 11/1984 | Japan . |
| 61-106501 | 5/1986 | Japan . |
| 8903178 | 4/1989 | WIPO . |
| 9105472 | 5/1989 | WIPO . |
| 9105471 | 5/1991 | WIPO . |

OTHER PUBLICATIONS

CA 102:127337 "Carboxylic Acid Amines As Herbicides," p. 225 (corresponds to JP 59199606, Nov. 12, 1984).

*Primary Examiner*—S. Mark Clardy
*Attorney, Agent, or Firm*—Saliwanchik, Lloyd & Saliwanchik

[57] ABSTRACT

The subject invention pertains to novel methods and compositions utilizing novel fatty acid salts which exhibit excellent herbicidal activity in controlling unwanted vegetation. The novel compositions and methods described here facilitate effective weed control using a water soluble salt of a fatty acid.

16 Claims, 3 Drawing Sheets

HERBICIDALLY-ACTIVE FATTY ACID SALTS

The subject application is a continuation of Ser. No. 08/458,546, filed Jun. 2, 1995 (now U.S. Pat. No. 5,703,019); which is a continuation of Ser. No. 08/385,218, filed Feb. 8, 1995 (abandoned); which is a continuation of Ser No. 07/796,161, filed Nov. 22, 1991 (abandoned).

BACKGROUND OF THE INVENTION

Weeds cost farmers billions of dollars annually in crop losses and in the expense of keeping weeds under control. Much of the cost of intertillage of row crops, maintenance of fallow, seedbed preparation, and seed cleaning is chargeable to weed control. Suppression of weeds along highways and railroad right-of-ways, and in irrigation ditches, navigation channels, yards, parks, grounds, and home gardens also is expensive. Ragweed pollen is the source of annual periodic distress to several million hayfever sufferers. Poison ivy, poison oak, poison sumac, nettles, thistles, sandburs, and puncturevine also bring pain to millions. Weeds also serve as hosts for other crop diseases as well as for insect pests.

The losses caused by weeds in agricultural production environments include decrease in crop yield, reduced crop quality, increased irrigation costs, increased harvesting costs, decreased land value, injury to livestock, and crop damage from insects and diseases harbored by the weeds.

Chemical herbicides have provided an effective method of weed control; however, the public has become concerned about the amount of residual chemicals which might be found in food, ground water, and the environment. Stringent new restrictions on the use of herbicides and the elimination of some effective herbicides from the market place could limit economical and effective options for controlling costly weeds. Additionally, the visually apparent phytotoxic effects of some systemic herbicides appear very slowly on the target weeds, so pesticide users often seek methods by which the apparent speed of action of the herbicide is increased.

Recently, salts of fatty acids, primarily sodium or potassium fatty acid salts, have been used commercially as pesticides. Compositions having excellent pesticidal properties which exploit these salts are available commercially from Safer, Inc., under the trademark SAFER INSECTICIDAL SOAP. A herbicidally active composition utilizing partially saponified fatty acids as the active ingredient is sold by Safer, Inc. under the trademark SHARPSHOOTER. These fatty acid compositions are effective, naturally occurring pesticides which have no known long term environmental effects. Although fatty acid salts have herbicidal activity, it would be desirable to provide an alternative composition having an unsaponified active ingredient while maintaining the environmental compatibility of the pesticide and reducing the eye and skin irritancy of the product.

U.S. Pat. Nos. 2,626,862; 4,975,110; and 5,035,741 describe certain fatty acid compositions useful as herbicides. These documents mention the use of salts of fatty acids. Specifically, "saponified" fatty acids are discussed. Saponification means "to form the sodium or potassium salt of a fatty acid." It stems from the soap making industry where animal fats (esters of fatty acids and glycerol) are hydrolyzed in sodium or potassium hydroxide to form the sodium or potassium salts of the fatty acids (soaps) and free glycerol. Mixing sodium or potassium hydroxide with a free fatty acid to form the salt is also called saponification. "Complete" saponification means that 100% of the fatty acid is converted to the salt; "partial" saponification means that <100% of the acid is converted to the salt. This means there is a mixture of the free fatty acid and the fatty acid salt. U.S. Pat. No. 4,975,110 indicates that the free fatty acid form is preferable to fatty acid salts for use as a herbicide. These patents also teach that the proper formulation of a fatty acid herbicide requires one or more surfactants.

BRIEF SUMMARY OF THE INVENTION

This invention concerns novel compositions and methods for selective or non-selective control of plants. We have discovered that application to weeds of aliphatic amine salts of one or more substituted (or unsubstituted) saturated (or unsaturated) fatty acids results in the effective control of a broad range of plants. The fatty acids of the subject invention can be from about C7 to about C20 and can be, for example, in the epoxide, cyclopropane, methylated, or hydroxylated forms. The fatty acid salts of the subject invention can be represented by the following formula:

$$R_1 Y_1 Y_2 COOR_2$$

wherein $R_1$=C6 to C19 saturated or unsaturated hydrocarbon, or an epoxide, or cyclopropane thereof $Y_1$=H, C1–C5 hydrocarbon, or hydroxyl at any position along $R_1$ $Y_2$=H, C1–C5 hydrocarbon, or hydroxyl at any position along $R_1$ $R_2$=a salt-forming moiety chosen from the group consisting of aliphatic amines which form cationic aliphatic ammonium compounds.

Specifically exemplified herein are saturated fatty acid salts of length C7 to C11. The use of the compositions described here, when used in the proportions and application rates set forth more fully hereinafter, results in an unexpected herbicidal effect. Further aspects of the subject invention are formulations and methods of formulating fatty acid herbicides which facilitate the preparation of fatty acid herbicidal compositions without the use of surfactants. Also disclosed are procedures for preventing the formation of fatty acid esters in a composition comprising a fatty acid and a compound having free hydroxyl groups.

DETAILED DESCRIPTION OF THE INVENTION

Figure 1:
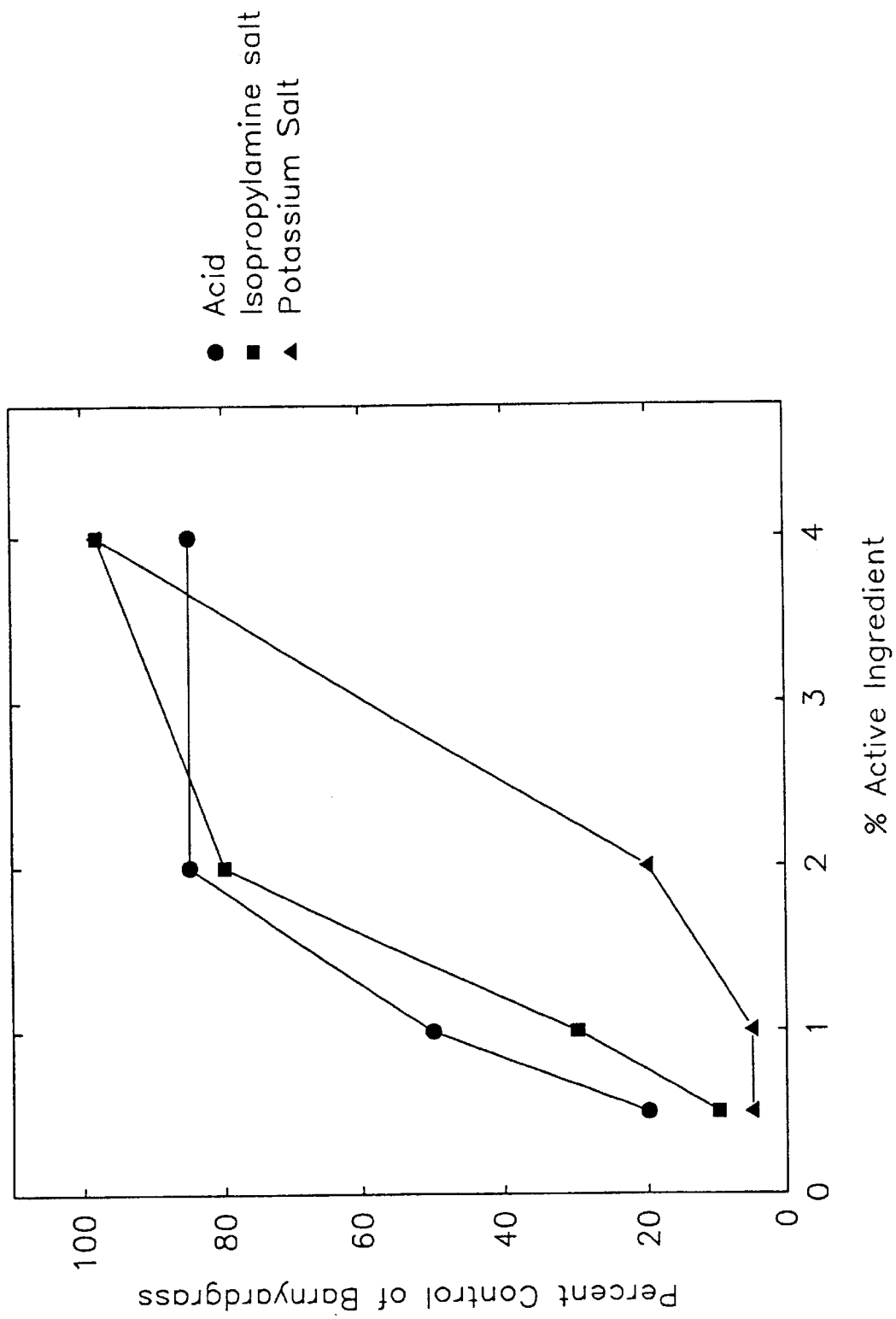
FIG. 1 shows control of barnyardgrass by various fatty acid compositions at a 100 gpa application rate.

The subject invention pertains to the discovery of certain fatty acid salts which have advantageous herbicidal properties. The herbicidal salts of the subject invention can overcome many of the difficulties described in the prior art pertaining to the herbicidal use of fatty acids. Specifically, the prior art taught that salts of fatty acids have reduced herbicidal activity compared to free acids and that the preferred herbicidal form was the free fatty acid rather than a salt. The prior art also taught that herbicidal preparations of fatty acids must be emulsions requiring one or more surfactants. It should be noted that the use of surfactants with fatty acid compositions presents difficulties because the surfactant must not undergo chemical reaction with the acid. Therefore, surfactants with free hydroxyl groups cannot be used due to the potential for formation of an ester between the fatty acid and the surfactant hydroxyl group. Thus, it has been necessary to use an ester or ether as a surfactant.

We have discovered that aliphatic amine salts of fatty acids have excellent herbicidal activity and overcome many of the problems which have heretofore limited the use of fatty acids as herbicides. The aliphatic amines of the subject invention are those which form cationic ammonium salts. Whereas potassium and sodium salts of fatty acids are not effective herbicides because of their substantially reduced herbicidal activity compared to the free fatty acid, the amine (ammonium) salts of the subject invention have excellent herbicidal activity and solubility characteristics. We have found that aliphatic amine salts of fatty acids have herbicidal activity very similar to the free fatty acids often can be formulated without the use of a surfactant. Thus, the aliphatic amine salts can be provided as a "ready-to-use" salt in water soluble form with or without addition of surfactants, or formulated as herbicidal concentrates with a variety of surfactants.

The fatty acid salts used according to the subject invention can be unsubstituted, or substituted, saturated, or unsaturated, fatty acid salts, of about C7 to about C20. Specifically exemplified are fatty acids of length C7 to C11, as typified by, but not limited to, decanoic acid or nonanoic acid. The fatty acid component of the subject invention may be a single fatty acid or a mixture of two or more fatty acids. The base used to form the salt can be an aliphatic amine or other compound which would form an essentially non-polar salt of a fatty acid. Aliphatic amines which may be used to form the salt of the subject invention can be selected from the group including, but not limited to, tryptamine, n-amylamine, ethanolamine, n-hexylamine, sec-butylamine, or isopropylamine. A preferred example is isopropylamine. Other organic amines (or non-amine organic bases) can be used according to the subject invention so long as these other bases have comparable attributes of base strength and polarity. Further examples of the compounds which can be used according to the subject invention include, but are not limited to, the alkyl amines, alkylene amines and alkanol amines containing not more than 2 amine groups, such as methylamine, ethylamine, n-propylamine, isopropylamine, n-butylamine, isobutylamine, sec-butylamine, n-amylamine, isoamylamine, hexylamine, heptylamine, octylamine, nonylamine, decylamine, undecylamine, dodecylamine, tridecylamine, tetradecyclamine, pentadecylamine, hexadecylamine, heptadecylamine, octadecylamine, methylethylamine, methylisopropylamine, methylhexylamine, methylnonylamine, methylpentadecylamine, methyloctadecylamine, ethylbutylamine, ethylheptylamine, ethyloctylamine, hexylheptylamine, hexyloctylamine, dimethylamine, diethylamine, di-n-propylamine, diisopropylamine, di-n-amylamine, diisoamylamine, dihexylamine, diheptylamine, dioctylamine, trimethylamine, triethylamine, tri-n-propylamine, triisopropylamine, tri-n-butylamine, triisobutylamine, tri-sec-butylamine, tri-n-amylamine, ethanolamine, n-propanolamine, isopropanolamine, diethanolamine, N,N-diethylethanolamine, N-ethylpropanolamine, N-butylethanolamine, allylamine, n-butenyl-2-amine, n-pentenyl-2-amine, n-hexenyl-2-amine, and proeylenediamine; primary aryl amines such as aniline, methoxyaniline, ethoxyaniline, o,m,p-toluidine, phenylenediamine, 2,4,6-tribromoaniline, benzidine, naphthylamine, o,m,p-chloroaniline, and the like; and hetrocyclic amines such as pyridine, morpholine, piperidine, pyrrolidine, indoline, azepine and the like. Further, the salts formed according to the subject invention can be, for example, from the group consisting of monoalkylammonium, dialkylammonium, trialkylammonium, monoalkenylammonium, dialkenylammonium, trialkenylammonium, monoaklynylammonium, dialkynylammonium, trialkynylammonium, monoalkanolammonium, dialkanolammonium, and trialkanolanuonium.

Following are examples which illustrate procedures, including the best mode, for practicing the invention. These examples should not be construed as limiting. All percentages are by weight and all solvent mixture proportions are by volume unless otherwise noted.

EXAMPLE 1

A ready-to use aqueous formulation of the isopropylamine salt of pelargonic (nonanoic) acid was prepared. The pelargonic acid was obtained as "EMERY 1202" from Quantum Chemical Corporation, Cincinnati, Ohio, and is a mixture of normal fatty acids of chain length 8, 9, and 10, with C9 being predominant. Various aqueous formulations were prepared with up to 20% active ingredient as the fatty acid and up to 6% isopropylamine, with the balance being water. The requisite amount of pelargonic acid was dispensed into an appropriate mixing vessel and the mixing initiated. The requisite amount of water was added to the acid and the acid dispersed into the water by mixing, thus forming a cloudy, unstable dispersion. Isopropylamine (ALDRICH Chemical Company, Milwaukee, Wis.) was added slowly, with continuous mixing, in sufficient quantity to bring the pH of the formulation to approximately 7.4–7.8. At this approximate pH the cloudy dispersion became translucent as the fatty acid isopropylamine salt became water soluble. By employing the proportions of acid to isopropylamine described here, formulations of up to about 75% fatty acid can be prepared by this method.

An aqueous formulation prepared as described above and containing 4% fatty acid and isopropylamine was applied to barnyardgrass and sicklepod plants. These plants had been grown in a greenhouse in a soil-less potting mix (PROMIX) to the 2–3 true leaf stage. The application was made using a hand-held atomizer (CROWN Industrial Sprayers, Hebron, Ill.), and the aqueous formulation was applied to run-off (approx. 250 gallons per acre). Two days after treatment the plants were completely killed by the application.

Although surfactants are not necessary according to the methods or compositions of the subject invention, the formulations described herein do not preclude the addition of surfactants. For example, a surfactant may be useful when utilizing certain organic amine salts with lower solubility characteristics than those specifically exemplified herein. Also, as would be readily apparent to a person skilled in the art, the exact pH needed for optimum solution may vary with the organic amine employed. The optimum pH could be readily determined by a person skilled in this art.

EXAMPLE 2

Greenhouse trials were carried out to demonstrate the herbicidal activity obtained by application of a fatty acid organic amine salt. Barnyardgrass was planted into 2×2 in pots in a soil-less potting mix (PROMIX) and was cultivated in a greenhouse maintained at daytime temperatures of 70–90RF, and was watered by sub-irrigation to maintain vigor. Plants were treated at the 2–3 true leaf stage.

Herbicidal concentrates of a free fatty acid, a saponified potassium salt, and an isopropylamine salt were prepared. Pelargonic acid was formulated according to mixing methods well known to practitioners in the art and using surfactants such as those disclosed in U.S. Pat. No. 4,975,110. Pelargonic acid was obtained as "EMERY 1202" from Quantum Chemical Corporation, Cincinnati, Ohio. An emulsifiable concentrate containing 60% by weight pelargonic acid was prepared in an emulsion system of 9% by weight "BRIJ 58" (ICI AMERICAS, INC, Wilmington, Del.), 0.5% by weight "RENNEX-31" (ICI), with the balance being ethylene glycol. A potassium salt concentrate was prepared as above, but contained approximately 20% by weight KOH with the ethylene glycol adjusted accordingly. An isopropylamine salt was likewise prepared with approximately 16% by weight isopropylamine with the ethylene glycol adjusted accordingly. A quantity of each of these 60% fatty acid concentrates was diluted with sufficient water to prepare an aqueous mixture containing 4% active ingredient calculated as the fatty acid. These mixtures, and appropriate dilutions thereof, were applied to barnyardgrass plants using a track sprayer calibrated to deliver the field equivalent of an application rate of 100 gallons per acre (gpa). After treatment the plants were removed to the greenhouse and maintained under good growth conditions.

At 4 days after treatment (DAT), the plants were rated to determine herbicidal effects. Weed control ratings ascertained the extent of control, i.e., reduction in growth, obtained and scored on the basis of 0 to 100 where 100 represents complete killing of the plants and 0 represents no reduction in growth, as compared to the untreated check.

FIG. 1 illustrates the weed control obtained with the free acid, and the loss of weed control typically observed when the free fatty acid is saponified, e.g., converted to the potassium salt. The isopropylamine salt produced a herbicidal effect more like that obtained with the free acid than that obtained with the saponified salt.

EXAMPLE 3

Another greenhouse trial was conducted to compare the isopropylamine salt to the free fatty acid at a low delivery volume (25 gpa). Barnyardgrass and sicklepod were cultivated in the greenhouse as described above. Plants were treated at the 2–3 true leaf stage. The free fatty acid and the isopropylamine salt mixtures were prepared in water by dilution of the appropriate concentrates, as described above, and applied to the plants in a track sprayer at the field equivalent of 25 gpa. After application, plants were returned to the greenhouse and maintained under good growing conditions. Herbicidal effects were assessed as described above at 4 DAT.

Figure 2:
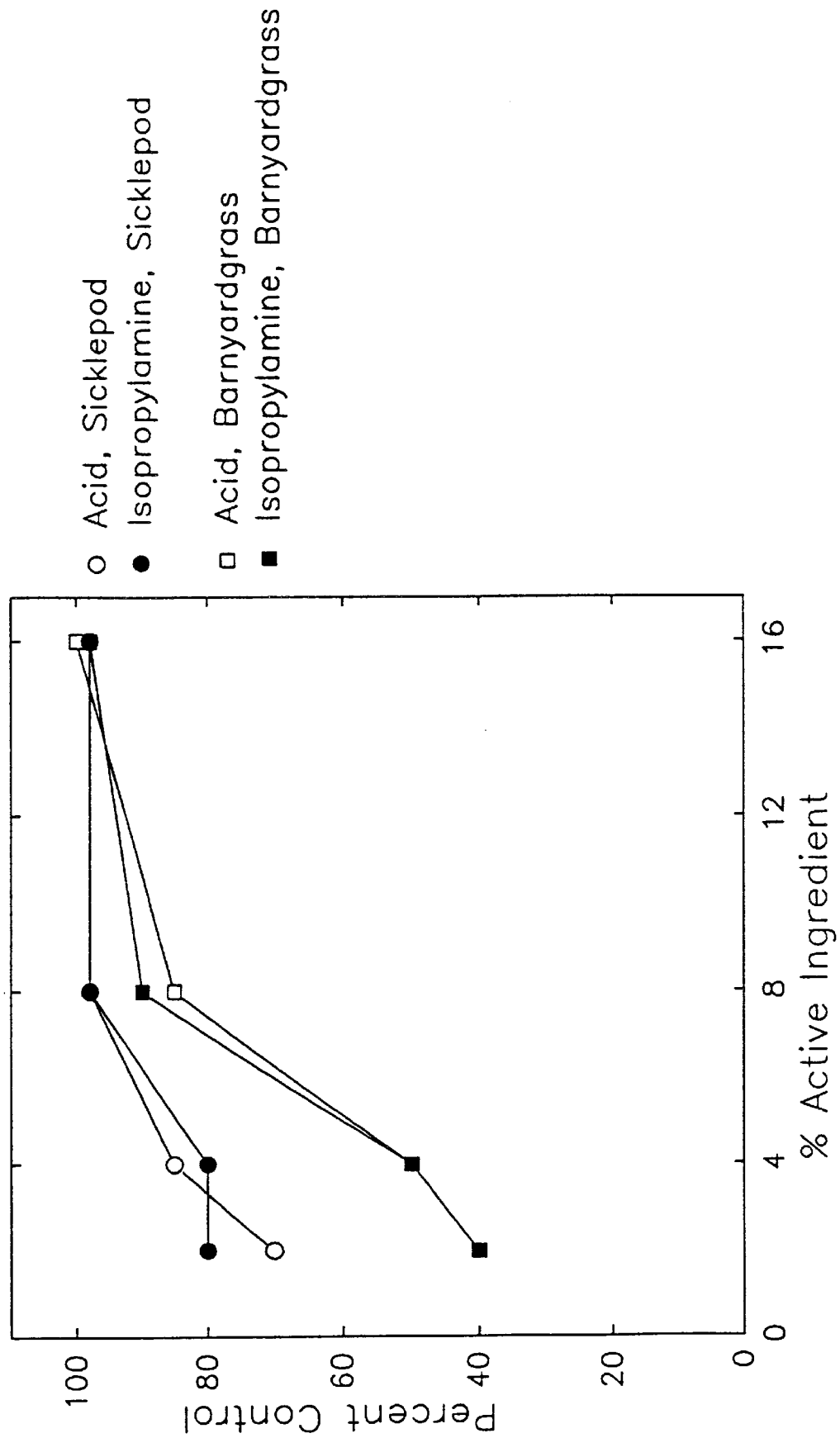
FIG. 2 shows control of sicklepod and barnyardgrass using either fatty acid or isopropylamine salt of fatty acid at 25 gpa application rate.

FIG. 2 illustrates the herbicidal effects of the free fatty acid and the isopropylamine salt on barnyardgrass and sicklepod at an application delivery rate of 25 gpa.

EXAMPLE 4

Greenhouse trials were carried out to demonstrate the herbicidal activity obtained following application of fatty acid salts of several organic amines. Florida beggarweed, velvetleaf, barnyardgrass, and crabgrass were used in these experiments. These weeds were planted in 2×2-inch pots in a soil-less potting mix (PROMIX) and were cultivated in greenhouses that were maintained at daytime temperatures of 70–90° F., and were watered by sub-irrigation to maintain vigor. Plants were treated at the 2–3 true leaf stage.

The fatty acid organic amine salt formulations were prepared by standard procedures similar to those described above, but with the following modifications: the sec-butylamine salt was approximately 19% by weight of the organic amine; the tryptamine salt, 20%; n-amylamine salt, 16%; n-hexylamine salt, 14%; and ethanolamine salt, 10%. Aqueous mixtures derived from these formulation concentrates were prepared at a 2% active ingredient rate, calculated as the free acid, by appropriate dilution in water. The test mixtures were applied to plants in a track sprayer delivering the field equivalent of 100 gpa. After application, plants were returned to the greenhouse and maintained under good growing conditions. Herbicidal effects were assessed as described above 4 DAT. Tables 1 and 2 show the herbicidal effects of the fatty acid organic amine salts.

TABLE 1

Weed control with 2% active ingredient solutions applied at 100 gpa

| | Percent Control | | |
| --- | --- | --- | --- |
| Formulation | Florida beggarweed | Velvetleaf | Barnyardgrass |
| Acid | 90 | 95 | 85 |
| Potassium salt | 50 | 20 | 20 |
| Isopropylamine salt | 90 | 90 | 80 |
| sec-Butylamine | 90 | 85 | 85 |

TABLE 2

Weed control with 2% active ingredient solutions applied at 100 gpa

| | Percent Control | | |
| --- | --- | --- | --- |
| Formulation | Florida beggarweed | Velvetleaf | Crabgrass |
| Acid | 100 | 100 | 98 |
| Tryptamine salt | 85 | 50 | 70 |
| n-amylamine salt | 100 | 90 | 90 |
| n-hexylamine salt | 100 | 100 | 95 |
| ethanolamine | 100 | 100 | 98 |

EXAMPLE 5

Figure 3:
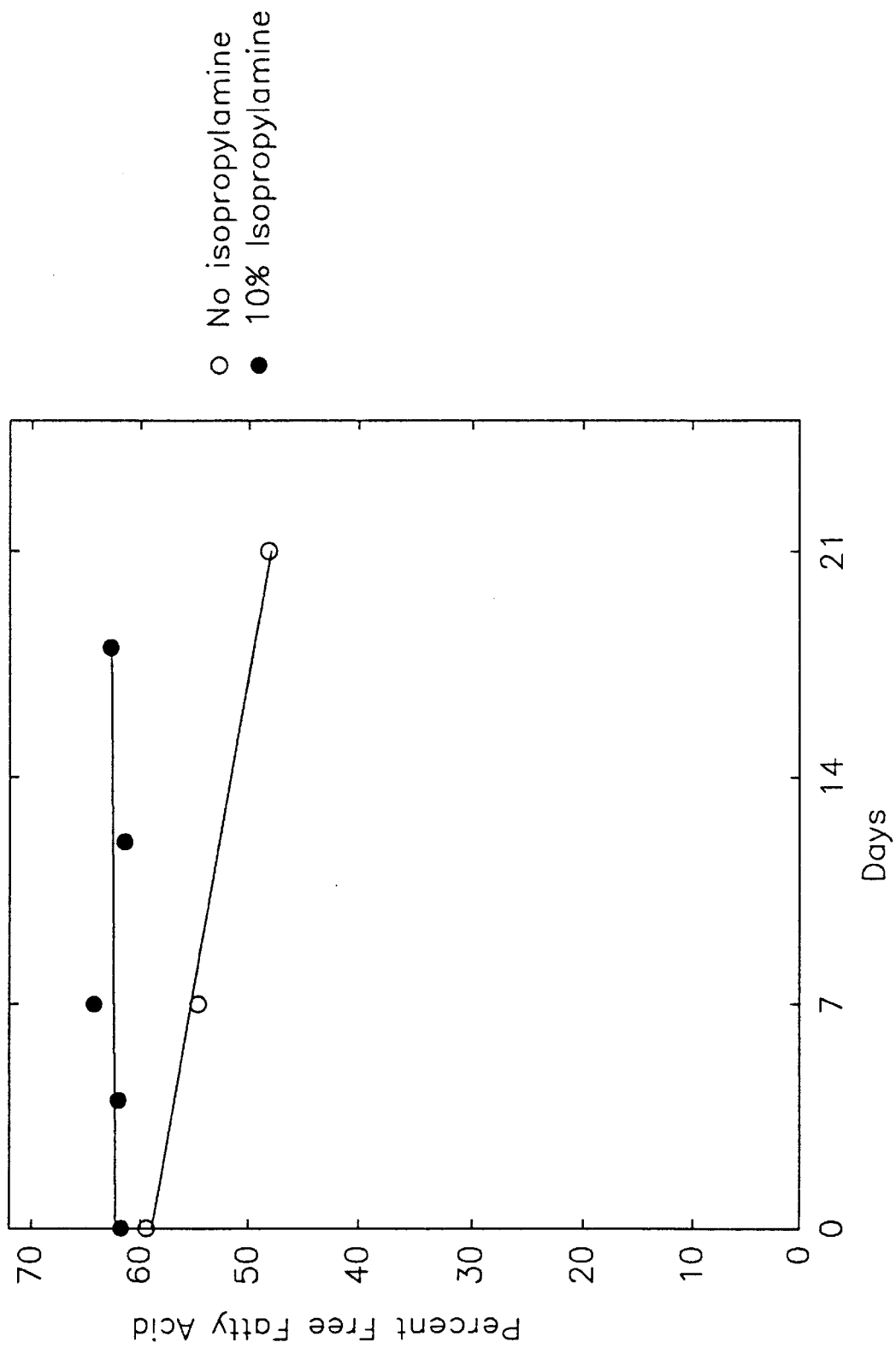
FIG. 3 shows the stability of a fatty acid in a formulation containing isopropylamine to prevent ester formation.

Herbicidal fatty acid emulsifiable concentrates were prepared in a solvent base containing ethylene glycol. The concentrates had as a base formulation, by weight, 60% pelargonic acid, 9% "BRIJ 58," 0.5% "RENNEX-31" (ICI) with the balance being ethylene glycol. As suggested in U.S. Pat. No. 4,975,110, over time the pelargonic acid was found to react with the hydroxyl groups of the ethylene glycol solvent to form the ethylene glycol ester of pelargonic acid. This reaction can be followed easily by base titration of the residual free fatty acid; as the ester forms, the amount of free fatty acid diminishes. The rate of reaction can be increased in accelerated stability studies performed at 40RC, and the combination of the titration method and the accelerated stability method can be used to evaluate modifications to the formulation which are made in an attempt to limit the amount of ester formed. A second emulsifiable concentrate was prepared as described above, but containing by weight, 60% pelargonic acid, 9% "BRIJ 58," 0.5% "RENNEX-31," 10% isopropylamine, 3% water, with the balance being ethylene glycol. FIG. 3 illustrates the stability of the fatty acid in a formulation containing isopropylamine to prevent ester formation. As can be seen from FIG. 3, the rate of ester formation from the fatty acid is substantially reduced when the organic amine is present.

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. A composition for controlling unwanted vegetation, wherein said composition comprises a suitable agricultural carrier and an organic monocarboxylic acid salt, wherein said monocarboxylic acid salt can be represented by the following formula:

$$R_1Y_1Y_2COOR_2$$

wherein $R_1$=C6 to C11 saturated hydrocarbon, or an epoxide, or cyclopropane thereof $Y_1$=H, C1–C5 hydrocarbon, or hydroxyl at any position along $R_1$ $Y_2$=H, C1–C5 hydrocarbon, or hydroxyl at any position along $R_1$ $R_2$=a salt-forming moiety chosen from the group consisting of a one- to seven-carbon amine and a one- to seven-carbon ammonium cation.

2. The composition, according to claim 1, wherein $R_1$ is C6 to C10.

3. The composition, according to claim 1, wherein $R_1$ is C9.

4. The composition, according to claim 1, wherein $R_1$ is C8.

5. The composition, according to claim 1, wherein said salt-forming moiety is selected from the group consisting of tryptamine, n-amylamine, ethanolamine, n-hexylamine, sec-butylamine, dimethylamine, and isopropylamine.

6. The composition, according to claim 5, wherein said salt-forming moiety is dimethylamine.

7. The composition, according to claim 5, wherein said salt-forming moiety is ethanolamine.

8. The composition, according to claim 5, wherein said salt-forming moiety is sec-butylamine.

9. The composition, according to claim 5, wherein said salt-forming moiety is methylamine.

10. The composition, according to claim 5, wherein said salt-forming moiety is isopropylamine.

11. The composition, according to claim 1, wherein said salt-forming moiety is an ammonium cation selected from the group consisting of monoalkylammonium, dialkylammonium, trialkylammonium, monoalkenylammonium, dialkenylammonium, trialkenylammonium, monoalkynylammonium, dialkynylammonium, trialkynylammonium, monoalkanolammonium, dialkanolammonium, and trialkanolammonium.

12. The composition, according to claim 1, which comprises a monocarboxylic acid salt according to the formula wherein $R_1$=C7, a monocarboxylic acid salt according to the formula wherein $R_1$=C8, and a monocarboxylic acid salt according to the formula wherein $R_1$=C9.

13. The composition, according to claim 12, which further comprises a surfactant.

14. The composition, according to claim 1, wherein said composition is in a concentrate form and comprises ethylene glycol.

15. The composition, according to claim 14, which further comprises a surfactant.

16. The composition, according to claim 1, which further comprises a surfactant.

* * * * *